US008845977B2

(12) United States Patent
Schmid et al.

(10) Patent No.: US 8,845,977 B2
(45) Date of Patent: Sep. 30, 2014

(54) APPARATUS FOR TRANSPORTING CONTAINERS

(75) Inventors: Manfred Schmid, Aufhausen (DE); Juergen Soellner, Beratzhausen (DE)

(73) Assignee: Krones AG (DE)

( * ) Notice: Subject to any disclaimer, the term of this patent is extended or adjusted under 35 U.S.C. 154(b) by 764 days.

(21) Appl. No.: 12/580,164

(22) Filed: Oct. 15, 2009

(65) Prior Publication Data

US 2010/0095637 A1 Apr. 22, 2010

(30) Foreign Application Priority Data

Oct. 16, 2008 (DE) ......................... 10 2008 052 002

(51) Int. Cl.
*A61L 2/00* (2006.01)
*B67C 7/00* (2006.01)
*B67C 3/22* (2006.01)

(52) U.S. Cl.
CPC ......... *B67C 7/0026* (2013.01); *B67C 2003/228* (2013.01)
USPC .............................. 422/304; 422/292; 53/425

(58) Field of Classification Search
CPC .................................. A61L 2/00; B65B 55/04
USPC ............................. 422/292, 300, 304; 53/425
See application file for complete search history.

(56) References Cited

U.S. PATENT DOCUMENTS

| | | | | |
|---|---|---|---|---|
| 3,783,581 | A | 1/1974 | Pierce | 53/37 |
| 3,863,658 | A * | 2/1975 | Kramb et al. | 134/131 |
| 5,406,772 | A | 4/1995 | Dinius | 53/67 |
| 7,250,145 | B1 * | 7/2007 | Miller et al. | 422/300 |

FOREIGN PATENT DOCUMENTS

| | | | |
|---|---|---|---|
| DE | 199 11 517 | 9/2000 | B67C 3/00 |
| GB | 2 280 669 | 2/1995 | B67C 7/00 |
| WO | WO 2006/029083 | 3/2006 | B65B 55/02 |

* cited by examiner

*Primary Examiner* — Sean E Conley
(74) *Attorney, Agent, or Firm* — Hayes Soloway P.C.

(57) ABSTRACT

An apparatus for transporting objects and in particular containers, having a first conveyor which transports the objects along a specified transport path (P), including a sterile room, within which the objects are transported, and including a second conveyor which follows on from the first conveyor. According to the invention, the first conveyor is positioned completely inside of the sterile room and the second conveyor is positioned completely outside of the sterile room, wherein both the first conveyor and the second conveyor are preferably positioned in a specified transitional area (B) along the transport path (P).

21 Claims, 4 Drawing Sheets

Fig. 4a
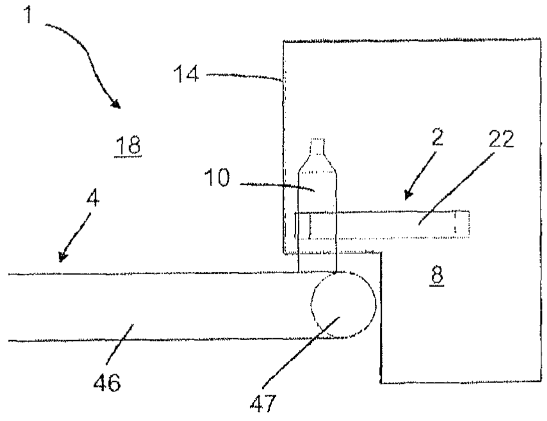
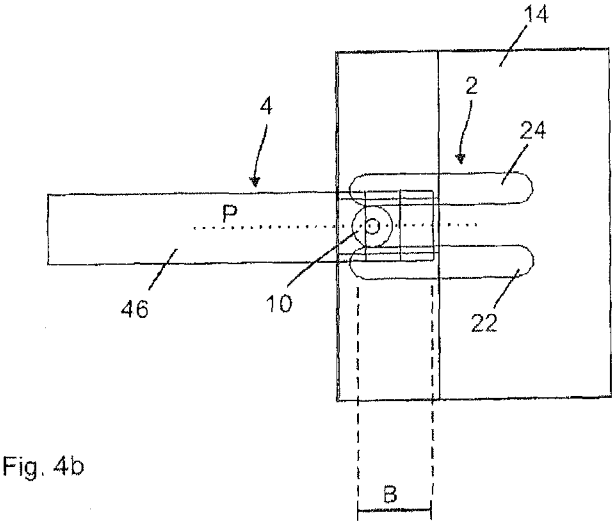
Fig. 4b

APPARATUS FOR TRANSPORTING CONTAINERS

BACKGROUND OF THE INVENTION

The present invention relates to an apparatus and a method for transporting objects and in particular containers. From the prior art, a number of different apparatus for treating objects and in particular containers are known. In this connection it is also known to treat such containers within a clean or sterile room and subsequently to transport them out of this sterile room. For example, it is possible that objects or containers are moved, more or less free-standing, supported by railings on generally customary conveyor belts, out of the sterile rooms or isolators. Thus, it is possible that the respective conveyor belt runs out of the sterile area via idle rollers and, thus, into and back out of the contaminated area. In this way it may occur that unsterile parts, such as for example unsterile parts of conveyor belts, find their way into the clean room and contaminate the latter.

From the Applicant's internal prior art a solution is known wherein an additional grey area is provided as a buffer between the sterile area and the surrounding area. Within this grey area, which like the sterile area also needs to be cleaned and disinfected, a push-over from a first belt to a second belt is incorporated. The first belt runs between the sterile area and the grey area and the second belt runs from the grey area towards the outside, which largely avoids a direct ingress of germs and impurities from the environment into the sterile area. Corresponding separating walls of the sterile room are usually positioned transversally to the transport direction of the containers here. A disadvantage of this approach is that the objects are more liable to fall over during the handover from one locker output spider onto the conveyor belt or on the push-over between the two conveyor belts, which in turn may result in interferences of the system operation.

The problem mentioned above is relevant for example in the case of aseptic filling devices, wherein containers filled under sterile conditions in a clean room are carried out of the clean room. In the grey room mentioned above (which acts as a sluice) between the sterile room and the unsterile environment, it is ensured by means of venting technology that air from the sterile zone flows into this grey room, by which means it is avoided that any germs from the environment will get into the clean room via this grey room. The positioning of this clean room thus results in an increased complexity, since it is necessary when establishing the pressure conditions in this clean room, to take into account both the sterile room and the non-sterile area. To ensure that air will not unnecessarily be lost from the clean room and that as little medium as possible gets into the environment during cleaning or disinfection of the clean room, the clean room will be sealed off transversely to the second belt mentioned, and this sealing off will be done by means of a flap which is closed during the cleaning and disinfection operations.

Since this flap, as mentioned above, is also located transversely to the outrunning belt, the space in the area of the exiting and returning outrunning chain cannot be sealed, so that the maximum workplace concentration (MAK) in the environment will be degraded and a lot of air is lost during production.

The present invention is therefore based on the object of simplifying corresponding transport systems for containers from sterile rooms or into sterile rooms. According to the invention, this is achieved by means of an apparatus according to claim 1 and a method according to claim 12. Advantageous embodiments and further developments are the subject matter of the dependent claims.

SUMMARY OF THE INVENTION

An apparatus according to the invention for transporting objects and in particular containers includes a first transport means which transports the objects along a specified transport path, as well as a sterile room within which the objects are transported. Further, the second transport means is provided which follows on from the first transport means.

According to the invention, the first transport means is positioned completely within the sterile room and the second transport means is positioned completely outside of the sterile room. Further, both the first transport means and the second transport means are positioned in a specified transitional area along the transport path. However, it would also be conceivable that the transport means immediately follow one another along the transport path.

Unlike the prior art, it is suggested according to the invention to position a transport means completely outside of the transport room and another one completely within the transport room. In this way it may avoided that any impurities are transported into the sterile room by a conveyor belt which extends from the sterile room into the environment.

The expression "complete positioning of the transport means inside or outside of the sterile room" is understood to mean that in particular those elements which come into contact with the objects or containers, or also the movable elements of the respected transport means, are allocated at all times either inside or outside of the sterile room. Thus, no mechanical movement will occur between the sterile room and the areas outside of the sterile room.

Preferably, a handover or transitional area is further provided, wherein both conveying means are positioned along the transport path. This means that the two conveying means intersect in this area, although one of them is positioned completely inside and the other one completely outside of the sterile room. For example, it is possible that in particular in a direction running perpendicularly to the transport path, the two conveying means intersect. For example, it is possible that the conveying means are positioned in the transitional area next to each other or parallel to each other. It is also possible that parts of the first conveying means and the second conveying means are located only partly in this transitional area. This will be explained in more detail with reference to the figures.

By means of the embodiment according to the invention it is also possible that a complete sealing of the sterile room during cleaning or disinfection operations can be carried out. In this way, also, the increasingly strict legislation with regard to MAK may be taken into account, without having to install complex suction devices to this end. It is further possible that an exit flap in the sterile room is automatically operated, without any operator intervention being necessary for this, so that processing time can be saved here.

Since the two conveyor belts are positioned either completely inside the sterile room or completely outside it, it is also possible to dispense with continuous disinfection operations in particular of the second conveyor means or the second conveyor belt, so that the overall construction is simplified and costs may be reduced. By this means, improved hygienic conditions will be established. Also the overall air consumption of the clean room will be markedly reduced, since the overflow surface at the push-over will be significantly reduced by the improved sealing means. Apart from that, also the accessibility of the system for maintenance and repair is improved.

In an advantageous embodiment, a separating device between the sterile room and a room positioned outside of the sterile room is provided, and this separating device extends in the transitional area at least over a section with respect to the transport path at an angle deviating from 90°. Since the corresponding housings or separating walls between the sterile room and the clean room extend vertically relative to the transport path in the prior art, it is suggested according to the invention to position such walls at a different angle, e.g. oblique or also along the transport path.

In this way, the transitional area between the two conveying means mentioned above may be achieved. Thus, an intentionally different design compared to a typical housing is suggested. Such an inclined wall may extend both in the plane of the transport path obliquely as well as in a plane perpendicularly thereto.

The apparatus is preferably an apparatus which conveys containers out of a sterile room. However, it would also be possible for the apparatus to relate to such systems wherein containers are transported into a sterile room. Due to the fact that in the case of the arrangement according to the invention the first conveying means is located completely within the sterile room and the second conveying means is located completely outside of the sterile room or in the unsterile zone, as mentioned above, there will be no mechanical exchange between the sterile and the unsterile zone.

An area from the bottom of the sterile room may be sealed off up to the top edge of the conveying means, e.g. statically, by means of metal sheets, since the second conveying means or the run-out belt no longer intersects the separation line. From the top, e.g. it can again be sealed off by means of an exiting flap, which in this design may be moved automatically, without putting any operating personnel at risk. The exiting flap is preferably located in this arrangement within a contact protection device of the machine.

The corresponding separating device (such as e.g. separating metal sheets) may be incorporated in this embodiment also preferably in the longitudinal direction of the run-out belts, so that the run-out may also be completely sealed off for cleaning or disinfection operations of the clean room.

Preferably, the second conveying means is disposed downstream of the first conveying means in the transport direction of the objects. Thus, this is preferably here an apparatus for transporting containers, e.g. not yet closed, filled containers, out of the sterile room.

In a further advantageous embodiment at least one conveying means is a powered conveyor means. Preferably both conveyor means are powered conveyor means. This means that the objects are actively conveyed through both conveyor means, not by the mere influence of forces or gravity or the like.

In a further advantageous embodiment, the conveying means is disposed in such a way that in the transitional area, the object is contacted by parts of both conveyor means. Thus, for example, it is known to move containers in such a way that they are wedged between two horizontally extending belts, which are powered at the same or at different circulating speeds. In the handover area it is possible that the container is contacted by a first belt of the first conveyor means and is contacted by a second belt located on the opposite side of the second conveyor means.

In this embodiment it is possible to keep the standing area stationary, which means that this is not moved. Since in this embodiment there will also be no push-over of the containers in a direction running at an angle relative to the transport path, the containers cannot fall over as a result of such a push-over. This is particularly advantageous in the case of high system throughputs.

Thus, it is possible in an embodiment that the containers are conveyed out of the sterile room by means of two pairs of belts. The handover may here be carried out for example by a closer outfeed star to the first belt pair, which will be immediately firmly grasped. During transport, it could be further supported by a stationary base plate. In this case, the separation between the sterile room and the unsterile room is preferably carried out by means of an oblique wall corresponding to the installation position of the deflection rollers of the respective belts or conveyor means.

In a further advantageous embodiment, at least one conveyor means has a conveyor belt which carries the objects by their bottoms. For instance, it is possible that a conveyor means is implemented with laterally disposed belts as the first conveyor means, and a conveyor belt carrying the containers by their bottoms, as a second conveyor means.

Preferably, however, at least one conveyor means and in particular the first conveyor means has two opposite conveyor belts, which carry the objects by their lateral wall, with the objects being disposed between the two conveyor belts.

In a further advantageous embodiment the apparatus has a carryover means which conveys the objects from the first conveyor means to the second conveyor means. This may, for example, be metal sheets disposed at an angle, along which the containers are carried at an angle with regard to the transport path and in particular at an angle with regard to the actual movement direction of the containers.

The present invention is further directed to a system for treating objects by means of an apparatus of the above described type, as well as means disposed in the sterile room for a sterile treatment of the objects. This may be, for example, a filling system which fills the containers under sterile conditions. Thus, the invention may be used particularly in the case of filling systems with high requirements in hygiene (strict hygiene requirements?) in an isolated design or with a clean room. The invention is suitable for all types of objects and in particular for all containers such as plastic bottles, glass bottles or cans. The system is in particular a continuously operated filling system and especially a continuously operated filling system in a carousel design. Its use would, however, also be conceivable in linear machines.

The present invention further relates to a method for treating objects and in particular containers. In this connection, in a first method step, the objects are treated inside a sterile room in a specified manner. Subsequently, the objects are transported upon treatment by means of a first conveyor means along a specified transport path. After that, the objects are transported by means of a second conveyor means following on from the first conveyor means along the specified transport path.

According to the invention, the objects are conveyed by means of the first conveyor means or parts of the latter exclusively inside of the sterile room and by means of the second conveyor means exclusively outside of the sterile room.

Thus, it is suggested by the method according to the invention that none of the conveyor means will change during circulation between areas with different hygienic requirements. The transport path is in particular a transport path running along a straight line, however, it would also be possible that the transport path has curved sections.

In a preferred method, both the first conveyor means and the second conveyor means are disposed in a specified transitional area along the transport path. Preferably, the containers are carried at least during a short period of time both by components of the first conveyor means and by components of the second conveyor means. However, it would also be possible to provide a handover means which actively or passively conveys the objects from the first conveyor means to the second conveyor means.

In a further advantageous method, the objects are transported in a specified transitional area via different surface areas of the objects. For example, it is possible that the first conveyor means conveys the objects along the lateral surfaces thereof and the second conveyor means conveys them along the bottom surface.

BRIEF DESCRIPTION OF THE DRAWINGS

Further advantages and embodiments will become evident from the attached drawings, wherein:

FIGS. 4*a*-4*d* show a third embodiment of an apparatus according to the invention.

DETAILED DESCRIPTION OF THE INVENTION

Figure 1:
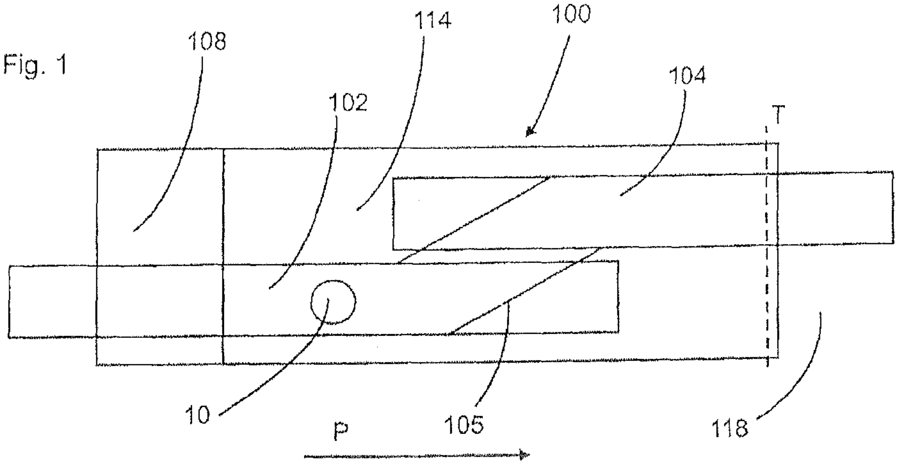
FIG. 1 shows a schematic view of an apparatus according to the prior art.

FIG. 1 shows a schematic view of an apparatus 100 according to the prior art. This apparatus 100 has a first conveyor means such as a conveyor belt 102 which transports containers 10 along a transport path P. This first conveyor means 102 is followed along the transport path P by a second conveyor means 104, which transports the containers 10 along the transport path P.

The reference numeral 108 relates to a sterile room within which the containers 10 are treated in a specified manner, for example are filled under sterile conditions. From this sterile room 108, the containers 10 are transported into a transitional or grey room 114, wherein on the one hand sterile conditions are prevailing, on the other hand impurities may enter.

The first conveyor belt 102 is thus disposed not completely in the sterile room, but also extends into the transitional or grey room 114. The further conveyor belt 104 transports the containers 10 from the grey room 114 out into the environment 118, in which no sterile conditions prevail. The reference numeral 10 here relates to a separation line between the sterile area and the unsterile area. Inside of this transitional area 114, disinfection nozzles may be provided, which clean the second conveyor means 104 and thus remove any impurities which may be carried into the grey room 114 via the conveyor means 104. Thus, in the case of the apparatus 1 known from the prior art a high degree of complexity is required in order to ensure that the actual sterile room 108 is kept sterile.

Figure 2:
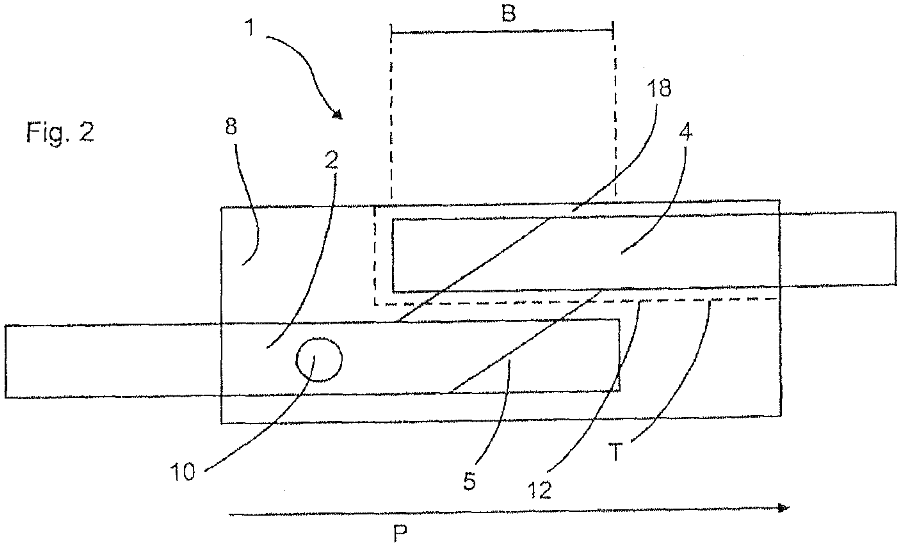
PRIOR ART Fig. 2
FIG. 2 shows a first embodiment of an apparatus according to the invention.

FIG. 2 shows an apparatus 1 according to the invention in a roughly schematic view. In this apparatus, too, there is a first conveyor means 2 which transports the containers 10 along the transport path P, as well as a second conveyor means 4 which transports the containers also along the transport path P. The essential difference between the apparatus according to FIG. 1 and the apparatus according to FIG. 2 is, however, that the first conveyor means is located completely inside of a sterile room 8, whereas the second conveyor means 4 is positioned completely outside of the sterile room 8.

A separation line T extends here between the two conveyor means 2 and 4. This may be, for example, a wall 12 which has only one opening through which the containers may get from the first conveyor means 2 to the second conveyor means 4. Thus, in this embodiment a separation line or wall 12 forming the separation line T extends along the path P. The two conveyor means 2, 4 are disposed here next to each other. The reference numeral 5 relates to a handover mechanism (disposed stationary), which carries the containers 10 from the first conveyor means 2 to the second conveyor means 4.

The reference numeral B characterises a transitional area in which both conveyor means 2, 4 are disposed along the transport path P. In this way, a transition of the containers 10 from the first conveyor means 2 to the second conveyor means 4 is enabled. It is possible here to position a flap in the wall, through which the containers 10 may enter from the sterile room 8 into the non-sterile room 18. There will preferably be a higher pressure within the sterile room 8 than outside of the sterile room 8.

In contrast to apparatus from the prior art, the housing wall 12 or the separation line will not extend perpendicularly to the transport path (see FIG. 1), but here in the direction of the transport path P.

Figure 3A:
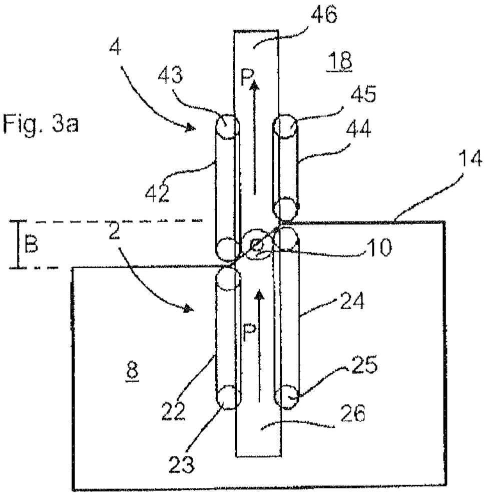
FIGS. 3*a*-3*d* show a second embodiment of an apparatus according to the invention.

FIG. 3*a* shows a second embodiment of an apparatus according to the invention. In this case, a housing 14 is provided, inside of which the sterile room 8 is formed. The first conveyor means 2 has here a transport plate 26 which is disposed stationary, as well as two lateral conveyor belts 22 and 24, between which the containers 10 are conveyed along the transport path P. The reference numerals 23 and 25 each relate to an idle roller of these two conveyor belts 22 and 24.

The first conveyor means 2 is followed here again by a second conveyor means 4, and this conveyor means 4 in turn has a conveyor plate 46 on which the containers 10 stand and in relation to which they are displaced, as well as two lateral conveyor belts 42 and 44, between which the containers 10 are conveyed. The reference numerals 43 and 45 identify again idle rollers of these lateral conveyor belts. It can be seen that here too a transitional area B is provided, in which the containers are handed over from the first conveyor means 2 to the second conveyor means 4. Or more accurately put, the containers 10 are here carried from the right-hand conveyor belt 24 of the first conveyor means and the left-hand conveyor belt 42 of the second conveyor means 4. The two conveyor belts 22 and 24 are positioned here completely inside of the sterile room 8 and the two conveyor belts 42 and 44 are positioned completely outside of the latter.

This arrangement makes it possible to implement the conveyor belts 42 and 44 (which are always located outside of the sterile room) in a conventional manner and to implement only the two conveyor belts 22 and 24 to be disinfected. Apart from that, it is possible here that a delimitation of the opening 13 of the housing 14 exactly follows the contour of the bottles. The prior art additionally also provided an opening which could not be closed within the housing of the conveyor means.

Figure 3B:
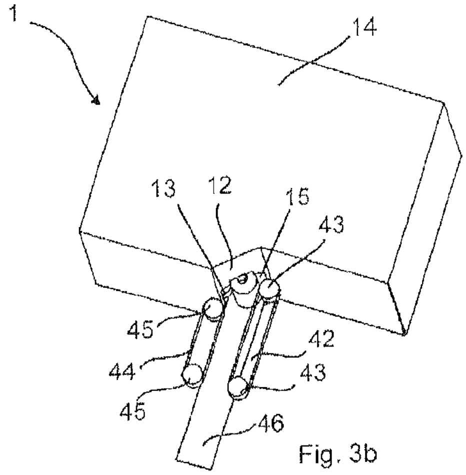

FIG. 3*b* shows a perspective view of the apparatus from FIG. 3*a*. It can be seen here that the housing 14 has a wall 12 running at an angle, which at the same time includes the border between the sterile and the non-sterile area. Preferably, there are higher pressure conditions inside of the housing 14 than outside of the housing, so that sterile air can always escape from the inside to the outside. The containers 10 are transported through an opening 13 in the wall 12 out of the housing 14 and thus out of the sterile room 8. In the case of the embodiment shown in FIGS. 3*a*-3*d*, the two base plates 26 and 46 are each disposed stationary. It would also be possible to use a continuous plate. The opening 13 in this embodiment acts as a sluice.

Figure 3C:
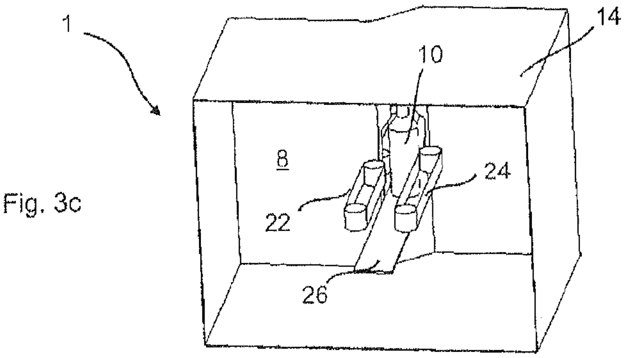
Figure 3D:
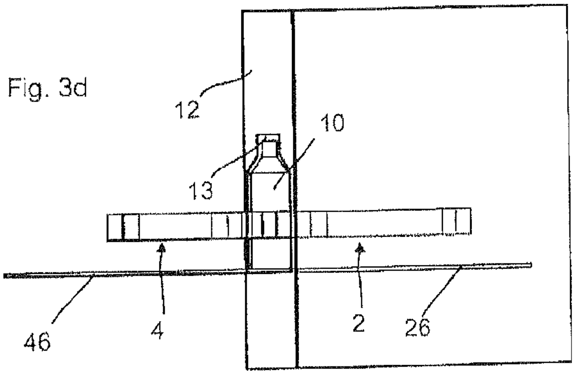

FIG. 3*c* shows an inside view of the apparatus shown in FIG. 3*b*. What can be seen here is the transport plate 26 of the first conveyor means 2 and again the two lateral belts or conveyor belts 22 and 24. FIG. 3*d* shows a further view of a corresponding apparatus. What can be seen here is that the two conveyor plates 26 and 46 are allocated at the same level and thus the containers 10 may get from the first conveyor means 2 to the second conveyor means 4 without a height offset. Also the respective conveyor belts 22, 24 or 42 and 44 are located at the same level here. However, it would also be possible to dispose the conveyor belts at different levels with regard to the containers 10.

FIG. 4*a* shows a further embodiment of an apparatus according to the invention. In the case of this apparatus, the first conveyor means 2 has lateral belts, such as in the case of the embodiment shown in FIGS. 3*a*-3*d*, but the second conveyor means 4 has a conveyor belt 46 extending in the horizontal plane. Thus the containers are transported through the first conveyor means by their outside circumference and on the second conveyor means 4 via their bottom surface.

However, also in the embodiment shown in FIGS. 4*a*-4*d* a handover area B is formed in which the container 10 is handed over from the first conveyor means 2 to the second conveyor means 4. The housing 14 is implemented here in a stepwise form, so that the second conveyor means 4 may geometrically reach into the transitional area, without however penetrating into the sterile area 8. The first conveyor means 2 may have here also a conveyor plate 26 (not shown in FIG. 4), on which the container 10 stands upright. However, it would also be possible that the containers 10 are carried in this area only through the two lateral belts 22 and 24.

Figure 4C:
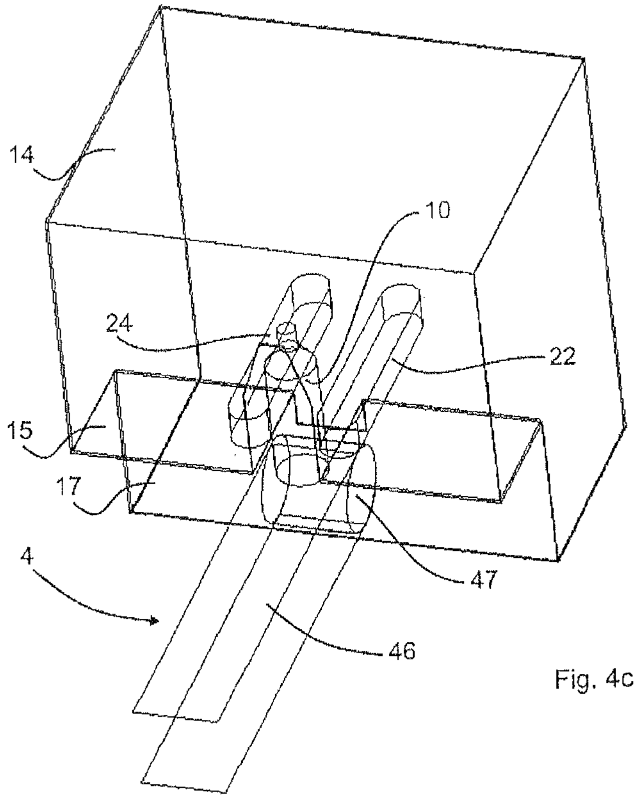

FIG. 4*c* shows a perspective view of the apparatus from FIGS. 4*a* and 4*b*. It can be seen here that the housing 14 has a wall 17 extending in a vertical direction and a wall extending in a horizontal direction. Both walls have openings here, through which the container 10 may be moved.

Figure 4D:
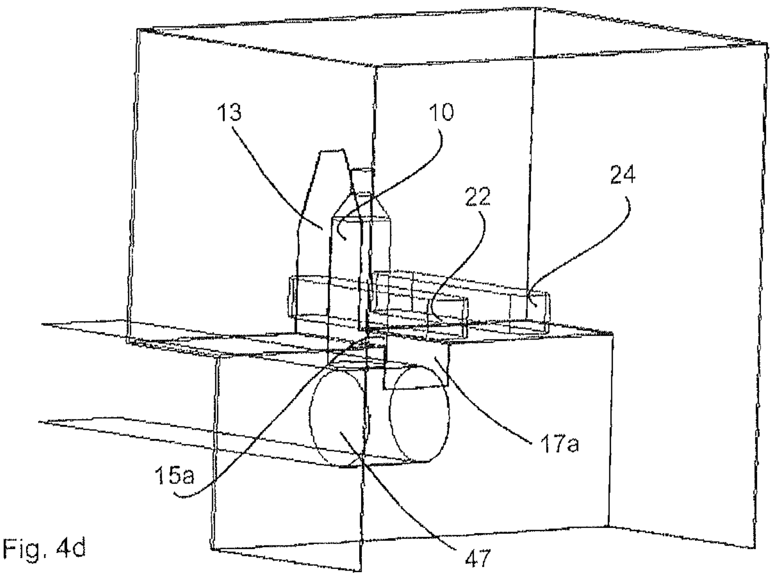

FIG. 4*d* shows a further view of the apparatus from FIG. 4*a*. In particular, an opening 17*a* may be seen here which is provided in the vertical wall 17, as well as an opening 15*a* which is located in the horizontal wall 15.

All of the features disclosed in the application documents are claimed here as essential to the invention, in as far as they are novel either individually or in combination compared to the prior art.

The invention claimed is:

1. An apparatus for transporting containers, including a first conveyor which transports the containers along a specified horizontal transport path (P), having a sterile room, through which the containers are transported, and having a second conveyor which follows on from the first conveyor, wherein the first conveyor is positioned completely inside of the sterile room and the second conveyor is located completely outside of the sterile room, wherein both the first conveyor and the second conveyor are disposed in a specified transitional area (B) along the transport path (P), and wherein an end of the first conveyor and an end of the second conveyor extend past one another and overlap horizontally in the transitional area, in which the containers are handed over from the first conveyor to the second conveyor.

2. The apparatus as claimed in claim 1, wherein a divider is provided between the sterile room and a room located outside of the sterile room and the divider extends in the transitional area (B) at least in sections with respect to the transport path (P) at an angle which deviates from 90°.

3. The apparatus as claimed in claim 1, wherein the second conveyor is positioned downstream of the first conveyor in the horizontal transport direction of the containers.

4. The apparatus as claimed in claim 1, wherein at least one conveyor is a powered conveyor.

5. The apparatus as claimed in claim 4, wherein both conveyors are powered conveyors.

6. The apparatus as claimed in claim 1, wherein both the first and second conveyors are disposed in such a way that the container will be contacted by parts of both conveyors in the transitional area (B).

7. The apparatus as claimed in at least claim 1, wherein at least one conveyor has a conveyor belt, which carries the containers by their bottoms.

8. The apparatus as claimed in claim 1, wherein at least one conveyor has two opposite conveyor belts which carry the objects by their lateral wall, with the objects being positioned between the two conveyor belts.

9. The apparatus as claimed in claim 1, wherein the apparatus has a handover, which conveys the containers from the first conveyor to the second conveyor.

10. The apparatus as claimed in claim 1, wherein both conveyors have a conveyor surface, which contacts the containers by their bottom surfaces.

11. System for treating objects using an apparatus as claimed in claim 1 and a sterilizing device disposed in the sterile room for a sterile treatment of the objects.

12. The apparatus as claimed in claim 1, wherein those elements which come into contact with the containers are allocated at all times either inside or outside the sterile room.

13. The apparatus as claimed in claim 1, wherein the movable elements of the two conveyors at all times are either inside or outside the sterile room.

14. The apparatus as claimed in claim 1, wherein the two conveyors run at a perpendicular angle to the transport path.

15. The apparatus as claimed in claim 9, wherein the handover comprises sheets disposed at an angle.

16. The apparatus as claimed in claim 1, wherein a separation line between the sterile room and the outside of the sterile room extends along the horizontal transport path of the containers.

17. The system as claimed in claim 11, wherein the system is a filling system for filling the containers under sterile conditions.

18. The apparatus as claimed in claim 1, wherein a separation line between the first conveyor and the second conveyor extends along the horizontal transport path of the conveyors.

19. An apparatus for transporting bottles or cans, including a first conveyor which transports the bottles or cans along a specified horizontal transport path (P), having a sterile room, through which the bottles or cans are transported, and having a second conveyor which follows on from the first conveyor, wherein the first conveyor is positioned completely inside of the sterile room and the second conveyor is located completely outside of the sterile room, wherein both the first conveyor and the second conveyor are disposed in a specified transitional area (B) along the transport path (P), and wherein and end of the first conveyor and end of the second conveyor extend past one another and overlap horizontally in the transitional area, in which the bottles or cans are handed over from the first conveyor to the second conveyor.

20. The apparatus as claimed in claim 1, wherein at least one conveyor has a conveyor surface, which contacts the bottles or cans by their bottom surfaces.

21. The apparatus as claimed in claim 11, further comprising a filling system for filling the bottles and cans under sterile conditions.

* * * * *